(12) United States Patent
Lyon

(10) Patent No.: US 9,001,620 B2
(45) Date of Patent: Apr. 7, 2015

(54) METHOD FOR ECHO PROCESSING IN A PULSE-ECHO RANGING SYSTEM

(75) Inventor: George Quinton Lyon, Peterborough (CA)

(73) Assignee: Siemens Aktiengesellschaft, Munich (DE)

( * ) Notice: Subject to any disclaimer, the term of this patent is extended or adjusted under 35 U.S.C. 154(b) by 520 days.

(21) Appl. No.: 13/345,342

(22) Filed: Jan. 6, 2012

(65) Prior Publication Data

US 2012/0201100 A1   Aug. 9, 2012

(30) Foreign Application Priority Data

Jan. 11, 2011   (EP) ..................... 11150662

(51) Int. Cl.
*G01S 15/08*   (2006.01)
*G01S 7/527*   (2006.01)
*G01F 23/284*  (2006.01)
*G01F 23/296*  (2006.01)
*G01S 7/292*   (2006.01)
*G01N 29/07*   (2006.01)
*G01N 29/44*   (2006.01)

(52) U.S. Cl.
CPC .............. *G01S 7/527* (2013.01); *G01F 23/284* (2013.01); *G01F 23/2962* (2013.01); *G01S 7/2922* (2013.01); *G01N 29/07* (2013.01); *G01N 29/4427* (2013.01); *G01N 2291/044* (2013.01)

(58) Field of Classification Search
USPC ...... 49/31; 73/1.82, 290 R, 304 R, 32 R, 582, 73/602, 618, 61.79, 625, 655, 861.25, 73/866.5, 290 V, 579, 587, 597, 598, 627, 73/632, 1.73; 118/712; 137/2; 141/83; 181/196; 209/173; 210/708; 219/109, 219/117.1; 244/134 C; 324/681; 333/252, 333/24 R; 340/870.02; 342/124, 173, 92; 343/753, 754, 786; 356/5.01; 361/54; 367/87–139, 65, 66, 69; 374/16, 5, 7; 378/4; 381/338; 382/100, 141; 420/528; 422/128, 68.1; 428/594; 429/50, 92, 93; 436/85; 600/369, 437, 600/438, 459; 702/39, 55, 56, 97, 14, 35, 702/40, 51, 54; 74/492
See application file for complete search history.

(56) References Cited

U.S. PATENT DOCUMENTS 3,435,227 A * 3/1969 Arazi ........................... 356/5.01
4,777,630 A * 10/1988 Burns ............................ 367/87
4,853,904 A * 8/1989 Pesque ......................... 367/89
(Continued)

FOREIGN PATENT DOCUMENTS

CN   1721875 A   1/2006
DE   197 04 220   8/1998
(Continued)

*Primary Examiner* — Isam Alsomiri
*Assistant Examiner* — Amienatta M Ndure Jobe
(74) *Attorney, Agent, or Firm* — Cozen O'Connor

(57) ABSTRACT

In a pulse-echo ranging system an energy pulse is transmitted to a target, echo pulses are received and converted into an echo signal that is processed to identify an echo from the target and to determine the distance from the propagation time of the identified echo, where the advanced stage of the processing is performed digitally. Instead of storing and processing the echo signal, the first derivative of the whole echo signal is stored in digital form and then processed to allow for storing as large a number of samples possible in a limited memory without reducing the resolution and without complicating the processing.

3 Claims, 5 Drawing Sheets

(56) References Cited

U.S. PATENT DOCUMENTS

| | | | |
|---|---|---|---|
| 5,436,580 A * | 7/1995 | Kellmann et al. | 327/24 |
| 5,793,705 A * | 8/1998 | Gazis et al. | 367/98 |
| 5,884,231 A * | 3/1999 | Perdue et al. | 702/28 |
| 5,946,967 A * | 9/1999 | Russell | 73/290 R |
| 6,047,602 A * | 4/2000 | Lynnworth | 73/632 |
| 6,330,831 B1 * | 12/2001 | Lynnworth et al. | 73/861.28 |
| 6,347,552 B1 * | 2/2002 | Purpura et al. | 73/633 |
| 8,446,796 B2 * | 5/2013 | Lyon | 367/88 |
| 2005/0072226 A1 * | 4/2005 | Pappas et al. | 73/290 V |
| 2005/0178198 A1 * | 8/2005 | Freger et al. | 73/290 V |
| 2006/0027021 A1 * | 2/2006 | Choi et al. | 73/579 |
| 2007/0068248 A1 * | 3/2007 | Freger et al. | 73/290 V |
| 2007/0165488 A1 * | 7/2007 | Wildey | 367/101 |
| 2008/0047329 A1 * | 2/2008 | Breed | 73/61.41 |
| 2008/0144440 A1 * | 6/2008 | Scoca et al. | 367/89 |
| 2008/0236275 A1 * | 10/2008 | Breed et al. | 73/290 V |
| 2008/0300490 A1 * | 12/2008 | Chiang et al. | 600/459 |
| 2010/0026984 A1 * | 2/2010 | Lewis | 356/5.01 |
| 2010/0223019 A1 * | 9/2010 | Griessbaum et al. | 702/75 |
| 2012/0201100 A1 * | 8/2012 | Lyon | 367/99 |

FOREIGN PATENT DOCUMENTS

| | | |
|---|---|---|
| DE | 19704220 A1 | 8/1998 |
| EP | 0 780 665 | 6/1997 |
| EP | 0780665 A2 | 6/1997 |
| JP | 2001091642 A | 4/2001 |

* cited by examiner

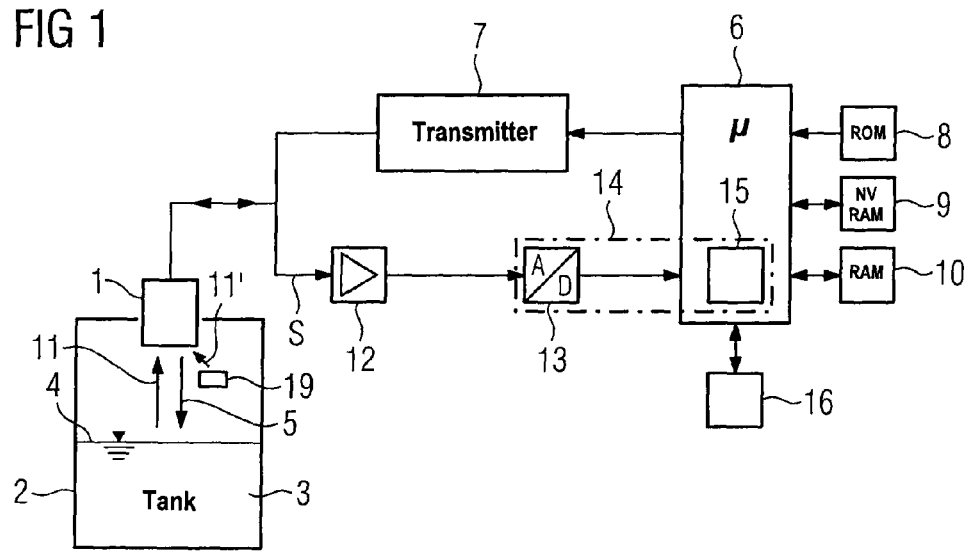
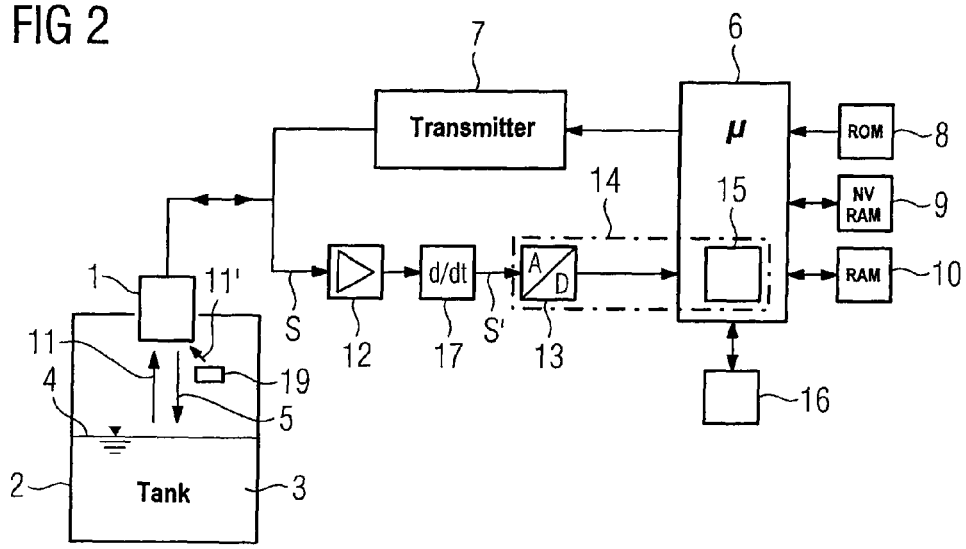

METHOD FOR ECHO PROCESSING IN A PULSE-ECHO RANGING SYSTEM

BACKGROUND OF THE INVENTION

1. Field of the Invention

The present invention relates to pulse-echo ranging system and, more particularly, to a method for echo processing in a pulse-echo ranging system, where the method comprises transmitting an energy pulse to a target, receiving echo pulses and converting them into an analog echo signal, and processing the analog echo signal to identify an echo from the target and determining the distance from the propagation time of the identified echo, where the advanced stage of the processing is performed digitally.

2. Description of the Related Art

In level measurement applications, pulse-echo ranging systems, which are also known as time-of-flight ranging systems, are commonly used for determining the distance to a target object (e.g., reflective surface of a material in a container) by measuring how long after transmission of an energy pulse the reflected pulse or echo is received. Such devices typically use ultrasonic pulses or pulsed radar or microwave signals.

In general, pulse-echo ranging systems include a transmitter for repeatedly transmitting the energy pulses and a receiver for receiving the reflected energy pulses or echoes. The transmitter and receiver may be combined in a single unit. The receiver provides an analog echo signal that contains any received echo, whether the received echo is from the target, or from clutter or noise. The echo signal may be amplified and/or filtered before it is digitized and stored as an echo profile. A signal processor identifies echoes of interest in the stored echo profile and calculates the distance or range of the target based on the transmit times of the transmitted energy pulses and the identified echo pulses.

A commonly used technique for finding echoes in an echo profile involves generating a time varying threshold (TVT) curve providing a line on the echo profile that is above the noise level in the echo profile. Valid echoes appear above the TVT curve. For identifying the echo of interest and determining its temporal position on a temporal axis, a variety of known techniques may be used, such as correlation or determining the echo's leading edge, trailing edge, peak or center of mass.

It is known from, for example, U.S. Pat. No. 5,436,580 to determine the beginning of an echo pulse within a received signal by developing a time dependent first derivative of the signal and comparing the signal with the derivative and with a reference threshold. Here, the leading edge of the echo pulse is indicated when the received signal exceeds both its derivative and the reference threshold.

In pulse-echo ranging systems, i.e., those having embedded microprocessors or microcomputers, the memory for storing the echo profile is limited, which limits the number of samples or their size (i.e., resolution) that can be stored. The worst case occurs when the measurement range is set to its maximum which means that the samples are furthest apart because the full range must now fit into the fixed size memory.

SUMMARY OF THE INVENTION

It is therefore an object of the present invention to provide a method that allows the storage of as large a number of samples as possible in a limited memory without reducing the resolution and without complicating the signal processing.

This and other objects and advantages are achieved in accordance with the invention by providing a method for echo processing in a pulse-echo ranging system in which a digitized and processed echo signal are further processed by performing intermediate steps of providing and storing the first derivative of the entire echo signal in digital form, and digitally processing the stored first derivative of the entire echo signal to identify the echo from the target.

As the sampling points are located near each other, the maximum difference between two adjacent samples is limited due to the given bandwidth of the echo signal. Thus, by storing, instead of the actual echo signal, its derivative or change, the resolution can be increased with unchanged memory requirements or the memory requirements can be reduced. Much of the echo processing, especially echo selection, can be performed directly on the derivative echo signal so that the echo processing will not be complicated by the fact that instead of the actual echo signal, its derivative is stored. The derivative contains all the important information contained in the original echo profile. As a result, echo processing on the derivative does not compromise the precision of distance measurement. (The offset information contained in the original profile is lost in the derivative but is not required for distance determination). Furthermore, the original echo profile can be recovered, wholly or in interesting sections, by simple integration.

The analog echo signal may be differentiated in an analog differentiator before it is digitized and stored for further processing. This has the advantage that the full conversion range of the analog to digital converter (ADC) is available for the limited maximum difference between two adjacent samples so that the resolution of the derivative of the echo signal in comparison to the original echo signal is improved. Alternatively, a smaller-sized ADC (e.g., 4-bit ADC instead of 8) can be used.

If it is preferred to implement the derivative without hardware changes, then the analog echo signal may be digitized and then digitally differentiated and stored.

Selection of the best echo by its amplitude, location, movement and other calculated parameters can be performed on the derivative as easily as on the original profile. The echo signal and thus its derivative may contain many echoes depending on the path travelled by the radar or ultrasonic energy pulse. Some criteria are applied to the echo signal to select the most appropriate echo. Some examples of the most likely echo are the largest echo, the first echo and the echo closest to previously measured echo. In a similar way, some echoes may need to be ignored even though they appear to meet some of the criteria for a valid echo; some examples are: known obstructions or echoes in the emitted beam's side lobes, electrically generated noise spikes, transient echoes such as those from a stirrer in a tank, and extremely narrow echoes.

In the differentiated signal, echoes are characterized by their accumulated amount of change. If the accumulated change is large, then an echo is present. Therefore, potential echoes may be identified by leaky-integrating the derivative of the echo signal, comparing the obtained integration values with a threshold and considering only those integration values that exceed the threshold. Integration values below the threshold may be set to zero. Clearly, a fixed threshold finds the wanted echo but it also finds other large signal portions, such as the transmit pulse. It is therefore advantageous to apply a variable threshold. The selection of such a variable threshold would be based on many parameters that a user could apply, for example, the presence of obstructions, the time dependent signal strength, the known noise levels and many more. The most basic variable threshold can be implemented as several different threshold values in a lookup table. The threshold can further be adjusted upon detection of an echo; e.g. it rapidly rises to become less sensitive after the echo is detected and then slowly decays with time.

In a variant of the method of the invention the potential echoes are identified by providing a variable threshold which is inversely proportional to the moving average of the derivative of the echo signal, comparing the derivative of the echo signal with the threshold and considering only the values which exceed the threshold. The threshold blocks small random noise but passes large continuously deviations which are related to echoes.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The invention will be now described in more detail with reference to preferred embodiments shown by way of non-limiting example in the attached drawings, in which:

FIG. 1 is a schematic block diagram of an embodiment of a pulse-echo ranging system in which the method of the invention may be advantageously implemented;

FIG. 2 is a block diagram of a pulse-echo ranging system in accordance with an alternative embodiment of the invention;

DETAILED DESCRIPTION OF THE PRESENTLY PREFERRED EMBODIMENTS

Figure 3:
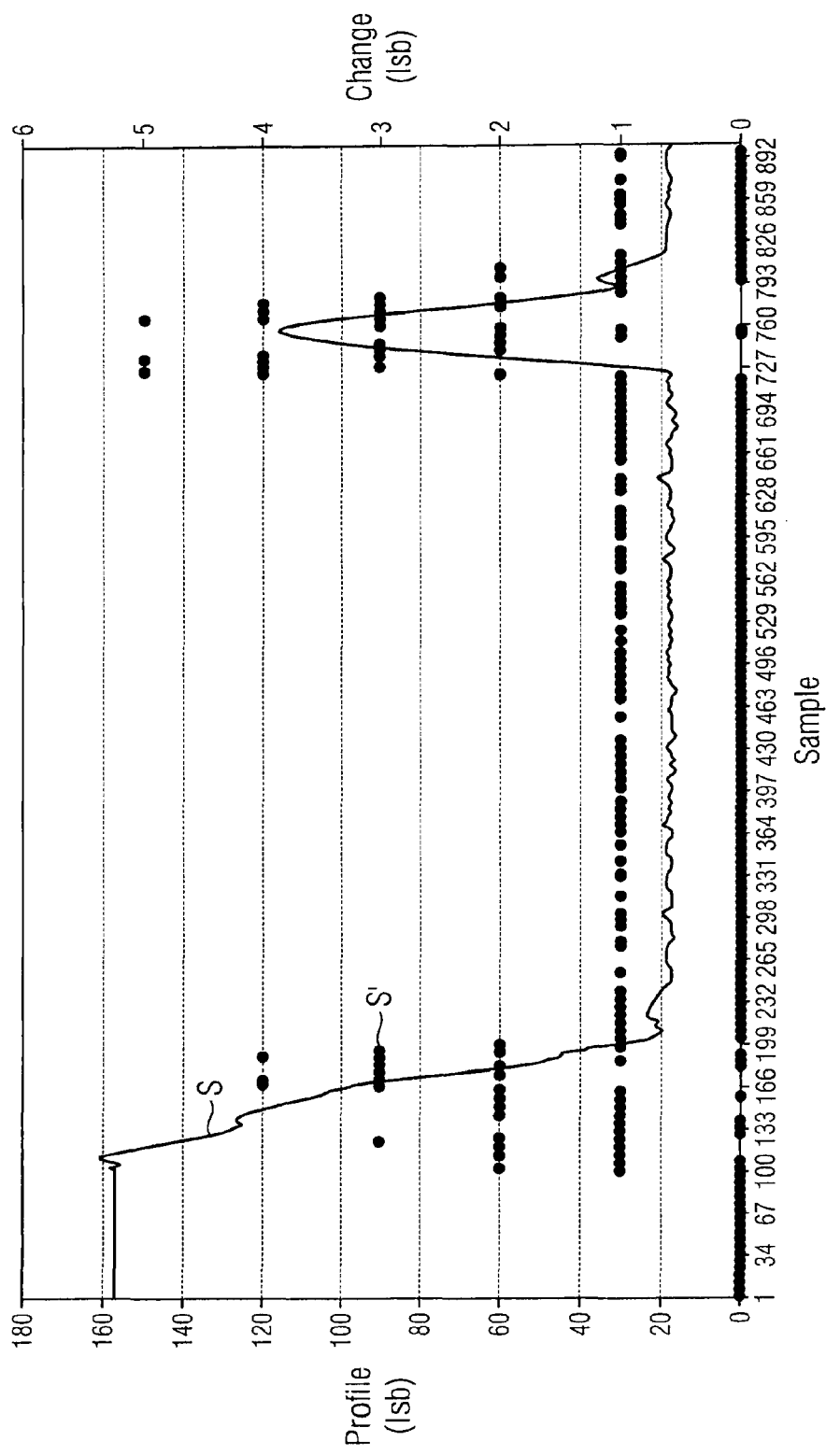
FIG. 3 shows is a graphical plot of an exemplary conventionally digitized echo signal and the magnitude of its change or derivative.

With specific reference to FIG. 1, shown therein is an acoustic pulse-echo ranging system comprising an ultrasonic transducer 1 that is installed in a tank 2 containing a liquid 3, or other type of material, with a level determined by the top surface 4 of the liquid 3. The top surface 4 of the liquid 3 provides a reflective surface that reflects ultrasonic pulses 5 generated by the transducer 1. The transducer 1 is coupled to a microprocessor 6 through a transmitter 7. The microprocessor 6 operates under a control program stored in read-only memory (ROM) 8, utilizing parameters stored in non-volatile random access memory (NVRAM) 9, and provided with a working memory in the form of random access memory (RAM) 10.

The microprocessor 6 controls the transmitter 7 to excite the transducer 1 to emit the ultrasonic pulses 5 at predetermined points in time and with predetermined frequency and amplitude. The reflected or echo pulse 11 is received by the transducer 1 and converted to an electric echo signal S which may be first amplified and band-pass filtered in an amplifier/filter 12 before it is sampled and digitized by an analog-to-digital converter (ADC) 13. The analog-to-digital converter 13 supplies digital values to the microprocessor 6 which then calculates the derivative by simple subtraction or a more refined method using more than two values for filtering out excessive noise. The digital difference values in their entirety form the first derivative of the entire echo signal S and are stored in the RAM 10. The analog-to-digital converter 13 is an input portion of a digital receiver 14 whose remaining portion is implemented in the microprocessor 6 as software modules 15. As will be described below, the microprocessor 6 executes an algorithm on the stored derivative of the echo signal S to determine the echo distance or time-of-flight and thus the level of the liquid 3 in the tank 2. An interface 16, controlled by the microprocessor 6, provides for the export of level-related data and the import of operating parameters. Data may be exported in the form of a display, telemetry (e.g., bus) signals, and/or alarm signals.

FIG. 2 shows an alternative embodiment of the acoustic pulse-echo ranging system that differs from that of FIG. 1 in that the analog echo signal S is differentiated in a differentiator 17 and then digitized and stored.

While the system and its operation are so far described in the context of an ultrasonic based pulse-echo acoustic ranging device, it should be understood that the system can also be radar based. The following examples are derived from or relate to a radar based system.

FIG. 3 shows an example of a conventionally digitized echo signal (echo profile) S and the magnitude (absolute values) of its change S'. The signal S is sampled with an 8-bit ADC and has a range of about 15 to 160 lsb which is about 60% of the full dynamic range of the ADC. This allows some leeway above and below the signal S for variations in signal strength and noise floor. The data points of the signal S are so near each other that the maximum difference between two adjacent samples is only +/−5 or 6 lsb. For the 8-bit ADC the sample range is from 0 to 255 lsb and the uncertainty is 1 lsb. The amount of data used to store the signal S is unnecessarily high. If, instead of the actual signal S, its derivative S' is stored the resolution can be increased by 16 times or the amount of storage used can be halved. Data compaction may be realized by sampling the derivative of the profile with a 4-bit ADC or storing only 4 bits of an 8-bit ADC. Thus, placing two samples of the derivative S' in each byte will use only half the space required for a normal signal S with no loss in precision. A 4-bit sample with a maximum change of ±5 lsb will not fully utilize the 4 bit dynamic range of 0 to 15 lsb, again allowing a generous 40% margin for noise and signal strength variation.

In the derivative of the echo signal S', echoes are characterized by their accumulated amount of change. If the accumulated change is large, then an echo is present.

Figure 4:
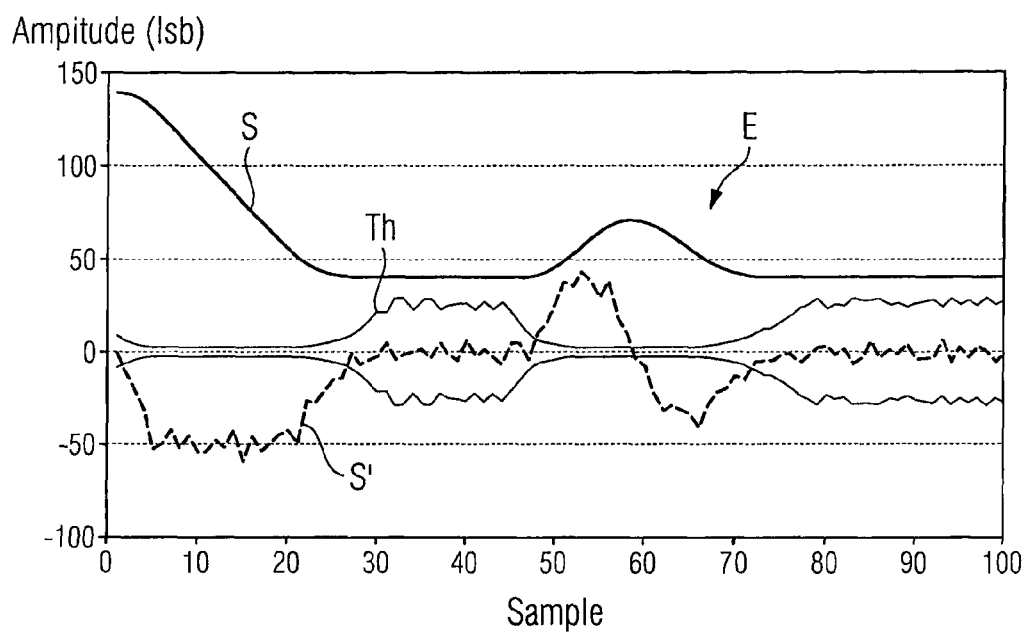
FIG. 4 is a graphical plot of a method for identifying a potential echo by providing a variable threshold that is inversely proportional to a moving average of the derivative of the echo signal.

As shown in FIG. 4, a potential echo E may be identified and extracted from the derivative signal S' by providing a variable threshold Th which is inversely proportional to the moving average of the derivative of the echo signal S', comparing the derivative of the echo signal S with the threshold Th and considering only the values that exceed the threshold Th. The threshold Th blocks small random noise but passes large continuously deviations which are related to echoes. The threshold Th may be defined in accordance with the relationship:

$$Th_i = \pm \frac{SF}{MA_i + \delta},$$

where $Th_i$ is the threshold value at sample point i, SF is a suitable scale factor that may itself be time dependant, $\delta$ is a small noise limit which also prevents dividing by zero errors, and MA is a moving average $$MA_i = \frac{1}{n}\sum_{j=1}^{i+n-1} S'_j$$

having the length n.

Figure 5:
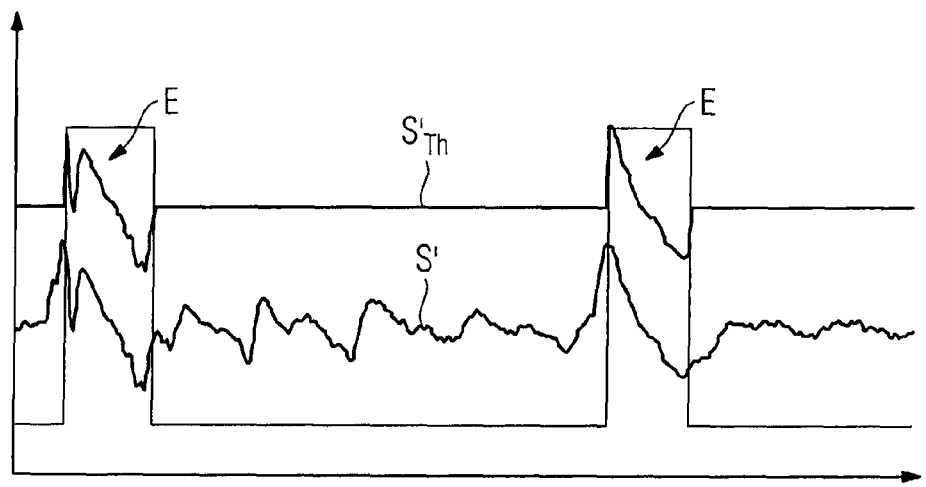
FIG. 5 is a graphical plot of a method for identifying a potential echo by performing a leaky-integration of the derivative of the echo signal and comparing the obtained integration values with a threshold.
Figure 6:
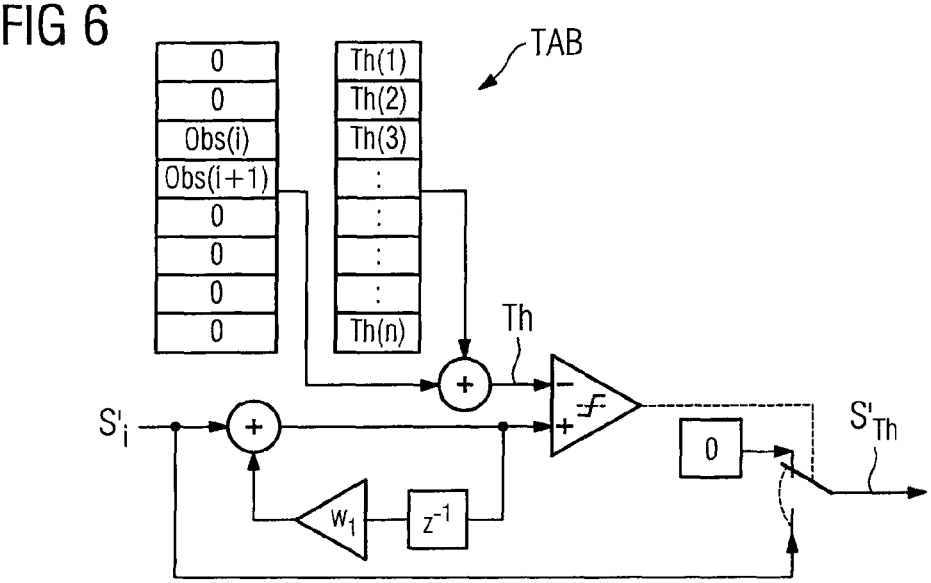
FIG. 6 is a schematic block diagram of a digital filter having a leaky-integrator and a comparator for performing the method in accordance with the invention.

FIGS. 5 and 6 show another example where potential echoes E are identified performing a leaky-integrating of the derivative signal S', comparing the obtained integration values with a threshold Th and considering only those integration values that exceed the threshold Th. Integration values below the threshold Th are set to zero so that a masked signal $S'_{th}$ is obtained. To distinguish between wanted echoes E and other large signal portions, such as the transmit pulse 5, the threshold Th is variable and implemented as several different threshold values (Th(i)) in a lookup table TAB. The selection of a suitable threshold value is based on many parameters that a user can apply, for example, the presence of obstructions (Obs(i)), the time dependent signal strengths, the known noise levels and many more.

Figure 7:
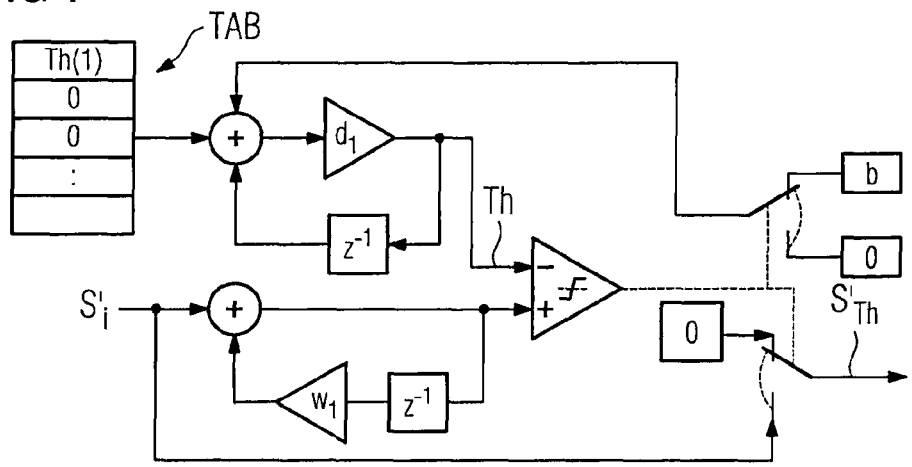
FIG. 7 is a schematic block diagram of a filter configured to increase the threshold in accordance with the method of the invention whenever an echo is detected and to then slowly reduce the threshold with time.

In the example of FIG. 7, the threshold Th is increased slightly by an amount b whenever an echo E is detected and slowly decays with time (d1<1) at all other times.

Figure 8:
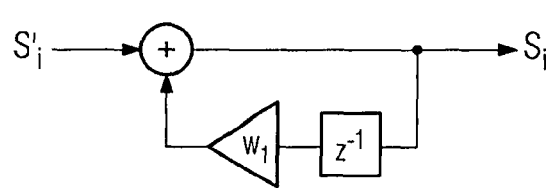
FIG. 8 is a schematic block diagram of a leaky integrator for reconstructing the echo signal or portions thereof from the derivative echo signal.

To implement known and trusted methods, sections of the echo signal (echo profile) of interest may be reconstructed from the stored derivative S'. FIG. 8 shows a simple first order reconstructor comprising a leaky integrator (W1<1). To increase the accuracy or to reduce the noise of the output signal, higher order filters may be provided.

Figure 9:
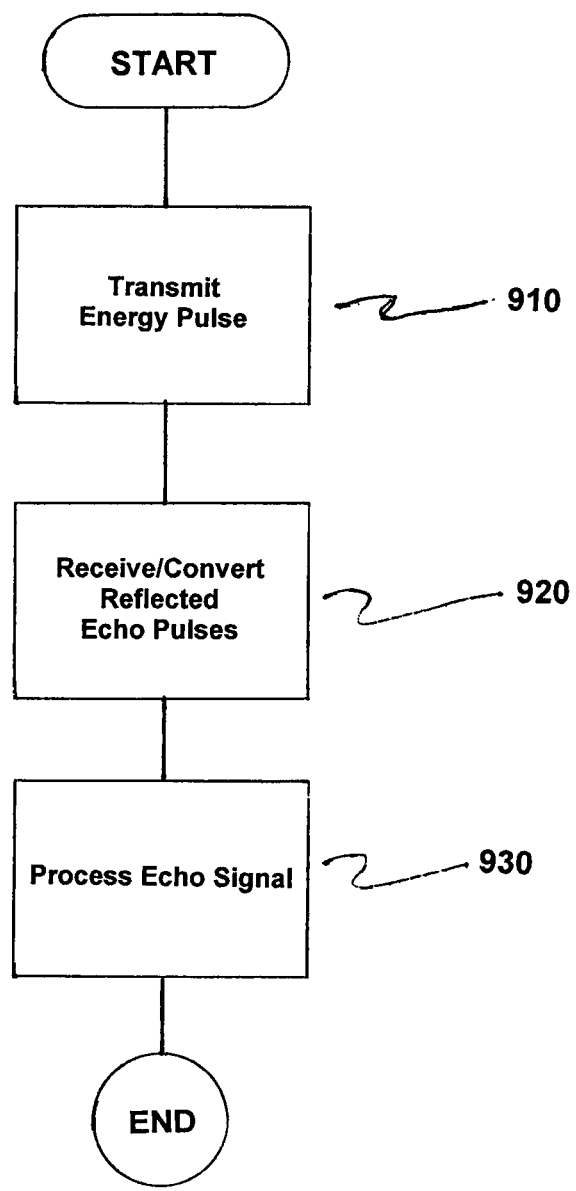
FIG. 9 is a flow chart of the method in accordance with an embodiment of the invention.

FIG. 9 is a flow chart of a method for echo processing in a pulse-echo ranging system. The method comprises transmitting an energy pulse to a target, as indicated in step 910. Echo pulses reflected from the target are received and converted into an analog echo signal, as indicated in step 920.

The analog echo signal is processed to identify an echo from the target and to determine a distance from a propagation time of the identified echo, as indicated in step 930. It should be noted that an advanced stage of processing is performed digitally, where the step of processing the analog echo signal further comprises providing and storing a first derivative of an entire echo signal in digital form and digitally processing the stored first derivative of the entire echo signal to identify the echo from the target.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those method steps which perform substantially the same function in substantially the same way to achieve the same results are within the scope of the invention. Moreover, it should be recognized that method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method for echo processing in a pulse-echo ranging system, the method comprising:
    transmitting an energy pulse to a target;
    receiving echo pulses reflected from the target and converting the received echo pulses into an analog echo signal;
    providing and storing a first derivative of an entirety of a digitized echo signal; and
    processing said first derivative of the entire digitized analog echo signal digitally to identify an echo from said target and determining a distance from a propagation time of the identified echo, an advanced stage of processing being performed digitally;
    wherein said step of providing and storing the first derivative of said entire digitized analog echo signal further comprises:
        sampling and digitizing, by an analog-to-digital converter, the analog echo signal;
        calculating the first derivative of the analog echo signal from digital sample values provided by the analog-to-digital converter by subtracting each adjacent ones of said digital sample values; and
        storing difference values obtained from each subtraction, or differentiating, in a differentiator, the analog echo signal;
        sampling and digitizing, by the analog-to-digital converter, the differentiated analog echo signal; and
        storing digitial sample values provided by the analog-to-digital converter.

2. The method according to claim 1, further comprising:
    performing a leaky-integration of the first derivative of the entire echo signal to identify potentially relevant echoes; and
    comparing obtained integration values with a threshold and considering only those integration values which exceed the threshold.

3. The method according to claim 1, further comprising:
    providing a variable threshold inversely proportional to a moving average of the first derivative of the entire echo signal to identify potential echoes; and
    comparing the first derivative of the entire echo signal with the threshold and considering only those values which exceed the threshold.

* * * * *